US005677276A

United States Patent [19]

Dickerson et al.

[11] Patent Number: 5,677,276

[45] Date of Patent: Oct. 14, 1997

[54] IMMOBILIZATION OF PEPTIDES TO HYALURONATE

[75] Inventors: Kenneth T. Dickerson, San Diego; James R. Glass, Cardiff; Lin-Shu Liu, Mountain View; James W. Polarek, Del Mar; William S. Craig, San Diego; Daniel G. Mullen, San Diego; Soan Cheng, San Diego, all of Calif.

[73] Assignee: La Jolla Cancer Research Foundation, La Jolla, Calif.

[21] Appl. No.: 469,582

[22] Filed: Jun. 5, 1995

Related U.S. Application Data

[63] Continuation of Ser. No. 363,213, Dec. 23, 1994.

[51] Int. Cl.$^6$ .......................... A61K 38/08; A61K 38/10; A61K 38/14; C07K 1/113

[52] U.S. Cl. .................................. 514/8; 514/13; 514/14; 514/15; 514/16; 514/17; 530/322; 530/326; 530/327; 530/328; 530/329; 530/330; 530/345; 530/411

[58] Field of Search .................................... 530/326, 327, 530/328, 329, 330, 322, 345, 395, 405, 406, 409, 411; 514/8, 13, 14, 15, 16, 17

[56] References Cited

U.S. PATENT DOCUMENTS

| | | | |
|---|---|---|---|
| 4,578,079 | 3/1986 | Ruoslahti et al. | 623/11 |
| 4,614,517 | 9/1986 | Ruoslahti et al. | 623/11 |
| 4,716,154 | 12/1987 | Malson | 514/54 |
| 4,792,525 | 12/1988 | Ruoslahti et al. | 435/240 |
| 4,879,237 | 11/1989 | Ruoslahti et al. | 435/240.2 |
| 4,963,666 | 10/1990 | Malson | 536/55.1 |
| 4,988,621 | 1/1991 | Ruoslahti et al. | 435/240.2 |
| 5,100,875 | 3/1992 | Marguerie de Rotrou | 514/18 |
| 5,120,829 | 6/1992 | Pierschbacher et al. | 530/326 |
| 5,310,881 | 5/1994 | Sakurai et al. | 530/395 |
| 5,330,911 | 7/1994 | Hubbell et al. | 435/240 |

FOREIGN PATENT DOCUMENTS

| | | |
|---|---|---|
| 6-80694 | 3/1994 | Japan . |
| WO86/00912 | 2/1986 | WIPO . |
| WO87/07898 | 12/1987 | WIPO . |
| WO89/05771 | 6/1989 | WIPO . |
| WO90/06767 | 6/1990 | WIPO . |

OTHER PUBLICATIONS

Maeda et al. Artificial Cell Adhesive Proteins . . . J. Biochem. 1991, vol. 110, pp. 381–387.

Wang et al., "New carbohydrate–based materials for the stabilization of proteins." *J. Am. Chem. Soc.*, 114:378 (1992).

Nilsson et al., "p–Toluenesulfonyl chloride as an activating agent of agarose for the preparation of immobilized affinity ligands and proteins. Optimizaiton of conditions for activation and coupling." *Acta Chem. Scand.*, 35:19 (1981).

Massia and Hubbell, "Covalent surface immobilization of Arg–Gly–Asp— and Tyr–Ile–Gly–Ser–Arg–containing peptides to obtain well–defined cell–adhesive substrates." *Analytical Biochem.*, 187:292 (1990).

Massia and Hubbell, "An RGD spacing of 440 nm is sufficient for integrin $\alpha_v\beta_3$–mediated fibroblast spreading and 140 nm for focal contact and stress fiber formation." *J. of Cell Biol.*, 114:1089 (1991).

(List continued on next page.)

*Primary Examiner*—Jeffrey E. Russel
*Attorney, Agent, or Firm*—Campbell & Flores LLP

[57] ABSTRACT

The present invention provides novel conjugates of a synthetic polypeptide containing RGD or (dR)GD and a biodegradable polymer, hyaluronate. The conjugates are prepared by any one of three different methods provided by the present invention: (1) an epoxide method (2) a sodium periodate method, and (3) a tresyl chloride method. The conjugates prepared by these methods are useful to aid in wound healing and tissue regeneration by providing a temporary matrix for tissue repair. The invention also provides novel RGD-peptides.

34 Claims, 5 Drawing Sheets

OTHER PUBLICATIONS

Massia and Hubbell, "Human endothelial cell interactions with surface-coupled adhesion peptides on a nonadhesive glass substrate and two polymeric biomaterials." *J. of Biomed. Materials Res.,* 25:223 (1991).

Andreassi et al., "Human keratinocytes cultured on membranes composed of benzyl ester of hyaluronic acid suitable for grafting." *Wounds,* 3:116 (1991).

Davidson et al., "Hyaluronate derivatives and their application to wound healing: Preliminary observations." *Clin. Mater.,* 8:171 (1991).

Andreassi L., "Treatment of burns with composite cultures of keratinocytes." *18th World Congress of Dermotology, New York,* 998–999 Jun. 12–18 (1992).

"Tresyl Activated Agarose" *Pierce Catalog & Handbook,* T363–T364 (1994–1995).

"Epoxy-activated" *Pierce Catalog & Handbook,* T365 (1994–1995).

"Carbonyl group coupling." *Pierce Catalog & Handbook,* T176 (1994–1995).

Hubbell et al., "Endothelial cell-selective materials for tissue engineering in the vascular graft via a new receptor." *Biotechnology,* 9:568–572 (1991).

Scott and Tigwell, "The influence of the intrapolymer environment of periodate oxidation of uronic acids in polyuronides and glycosaminoglycuronans." *Biochem. Society Transactions,* 3:662–664 (1975).

Aspinall and Ferrier, "A spectrophotometric method for the determination of periodate consumed during the oxidation of carbohydrates." *Chemistry and Industry,* 1216 (1957).

Sundberg and Porath, "Preparation of adsorbents for biospecific affinity chromatography," *J. of Chromatography,* 90:87–98 (1974).

Uy and Wold, "1,4-Butanediol diglycidyl ether coupling of carbohydrates to sepharose: affinity adsorbents for lectins and glycosidases." *Analytical Biochem.,* 81:98–107 (1977).

IMMOBILIZATION OF PEPTIDES TO HYALURONATE

This application is a continuation of application Ser. No. 08/363,213, filed Dec. 23, 1994.

BACKGROUND OF THE INVENTION

FIELD OF THE INVENTION

The present invention relates to peptides conjugated to hyaluronate polymers and methods for using the conjugates to promote the healing of wounds and tissue regeneration.

BACKGROUND INFORMATION

Slow wound healing, inappropriate wound healing, or lack of healing represent serious medical problems affecting millions of individuals. These problems occur in dermal wounds such as decubitus ulcers, severe burns and diabetic ulcers and eye lesions including dry eye and corneal ulcer, as well as surgical wounds. The healing of surgical wounds is particularly problematic for aging and diabetic individuals.

Although wounds may be quite dissimilar in terms of cause, morphology, and tissue affected, they share a common healing mechanism. In the wound healing process, tissue is replaced through the migration of cells and the synthesis of extracellular matrix by these cells. This repair process requires that the correct type of cell migrate into the wound in sufficient numbers to have a healing effect: macrophages to debride wounds, fibroblasts for the formation of extracellular matrix components in wounds where the extracellular matrix was damaged, capillary endothelial cells to promote angiogenesis and provide the blood supply, and epithelial cells to ultimately cover the wound.

The unwounded dermis owes much of its structure and strength to the interaction of cells with the extracellular matrix. The matrix contains proteins known to support the attachment of a wide variety of cells; fibronectin, vitronectin, thrombospondin, collagens and laminin are examples of matrix proteins. Plasma fibronectin deposition, for example, occurs at the wound site soon after wounding, although fibronectin is found in low concentrations in unwounded skin.

In addition to providing a scaffold for cell attachment and migration during wound healing, extracellular matrices also direct cellular proliferation and differentiation. Thus, matrix influences healing of a tissue in such a way that the correct tissue geometry is restored. When applied to wounds, exogenous fibronectin results in increased wound healing, epithelial migration and collagen deposition. However, fibronectin and other extracellular matrix proteins are less than ideal for treatment due to cost, availability and instability. In addition, as blood-derived products, extracellular matrix proteins may be vectors for infectious disease.

Cell growth factors, such as platelet derived growth factor (PDGF), fibroblast growth factor (FGF) or epidermal growth factor (EGF) also have been used to promote healing of dermis. However, growth factors primarily affect cell proliferation; when used alone, they do not confer the correct geometry of the new tissue, and can lead to overly vascularized tissue and abnormal healing. Moreover, it is known that an overabundance of growth factors such as TGF-β (transforming growth factor-β) and PDGF actually drive fibrosis, which in turn can impair successful healing. Additionally, many growth factors are known to be unstable and break down in topical or surface applications before a desired effect can be obtained.

It is now recognized that the binding domain of fibronectin and the other adhesion proteins is localized in the amino acid sequence Arg-Gly-Asp-X (also termed RGD-X, in accordance with the standard one letter abbreviations for the amino acids) wherein X can be various amino acids or substituents such that the peptide has cell adhesion promoting activity. Arg-Gly-Asp-containing peptides and their uses are disclosed, for example in the following issued United States patents: Pat. Nos. 4,578,079 and 4,614,517, 4,792,525, 4,879,237, and 5,120,829. From these discoveries, work has progressed in the generation of various Arg-Gly-Asp-containing peptides having various specificities for particular cell surface receptors.

Arg-Gly-Asp-containing peptides conjugated to biodegradable polymers, such as hyaluronate, are also known to be useful in promoting rapid healing of wounds. The biodegradable polymer functions as a support or scaffold for tissue repair when RGD-containing peptides are attached. There remains a need, however, to create scaffolds of increased residence time and alternative forms. As well, there is a need for increasing the coupling efficiency and the strength of the polypeptide-polymer bond. The present invention satisfies these needs and provides related advantages as well.

SUMMARY OF THE INVENTION

The present invention provides novel conjugates of a synthetic polypeptide containing RGD or (dR)GD and a biodegradable polymer, hyaluronate. The conjugates are prepared by any one of three different methods provided by the present invention: (1) an epoxide method (2) a sodium periodate method, and (3) a tresyl chloride method. The conjugates prepared by these methods are useful to aid in wound healing and tissue regeneration by providing a temporary matrix for tissue repair. The invention also provides novel RGD-peptides.

DETAILED DESCRIPTION OF THE INVENTION

The extracellular matrix of mammalian dermis contains several proteins known to support the attachment and promote the migration and differentiation of a wide variety of cells, including fibronectin, vitronectin, collagens and laminin. When the dermis is cut, burned or abraded, this extracellular matrix may be separated or lost. This matrix must be replaced before the wound can be repaired by cellular migration and replication because cells require the matrix to be in place before cell migration, and healing, can occur.

In natural wound healing, the tissue is replaced through the migration of cells and the synthesis of extracellular matrix by them. This process is time-consuming, often requiring more than one year to complete. The resulting tissue is scarred and is weaker than the surrounding, unwounded tissue.

The present invention provides stable "synthetic matrices" that can be used to support the healing of many different wounds by providing the cells with an attachment base for cell migration. The "synthetic matrix" comprises a conjugate of a biodegradable polymer and a peptide sequence that cells can use as a binding site during migration.

Figure 1:
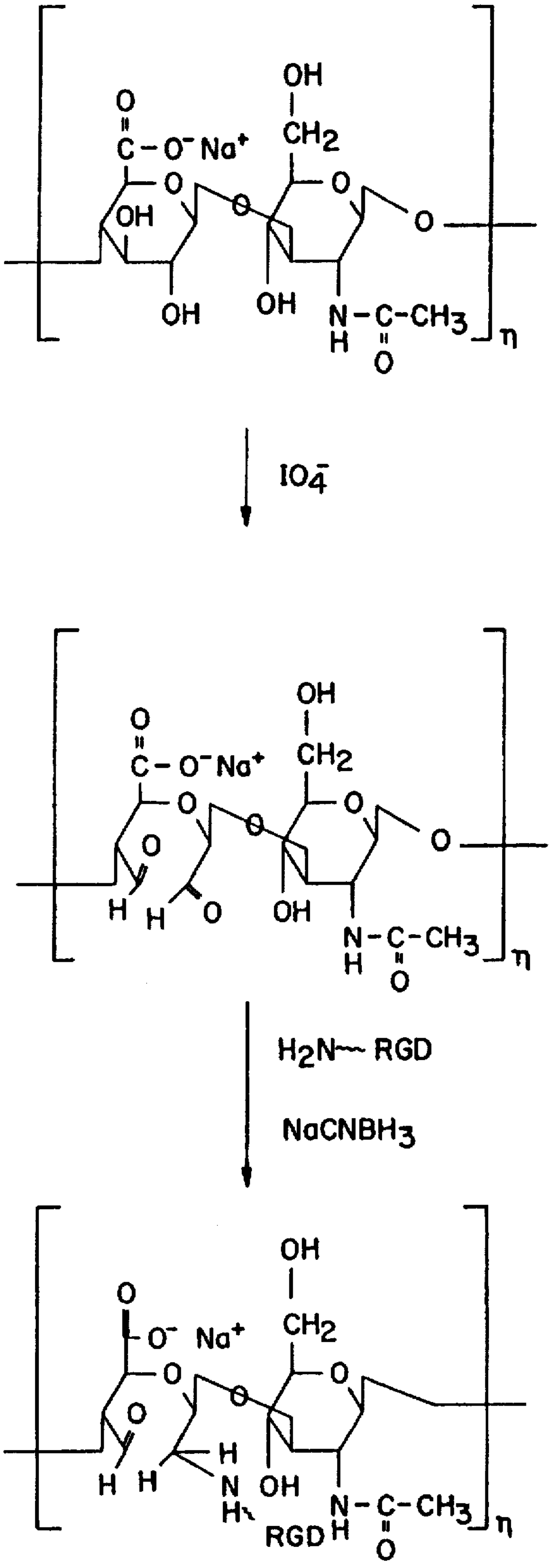
FIG. 1 provides a diagram exemplifying the coupling of an RGD-containing peptide to hyaluronate using the sodium periodate method.
Figure 2:
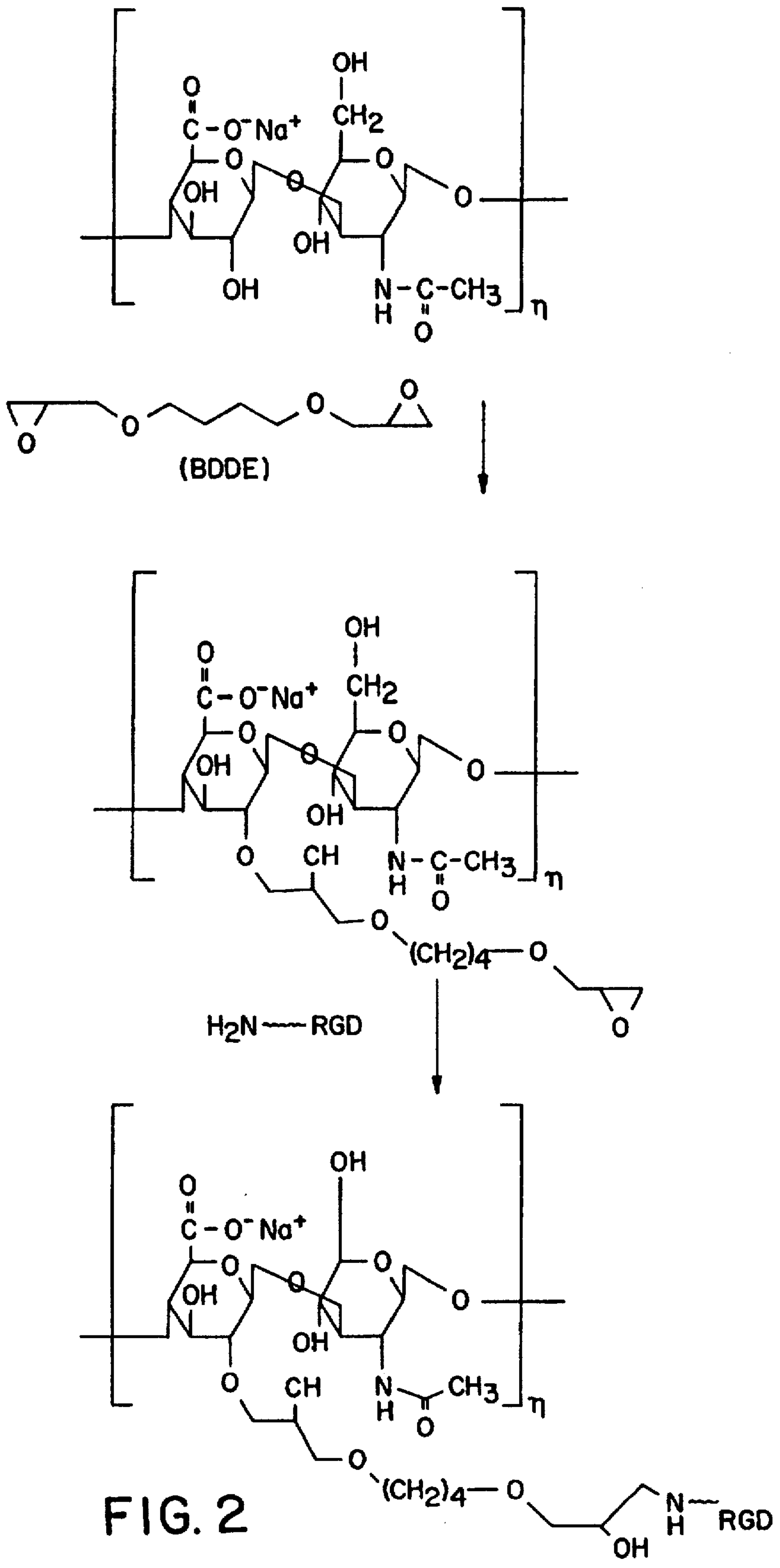
FIG. 2 diagrams an example of the chemistry involved for immobilizing an RGD-containing peptide to hyaluronate using the epoxide method with the reagent 1,4 butanediol diglycidyl ether (BDDE).
Figure 3:
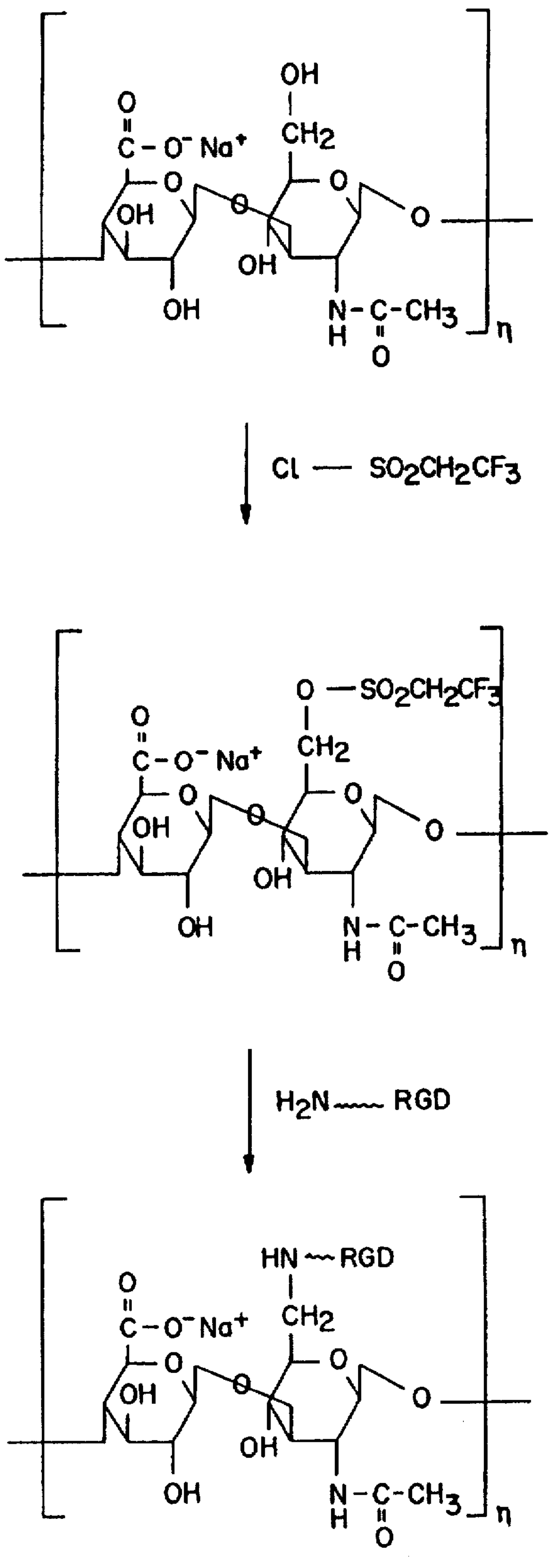
FIG. 3 provides an exemplary chemical reaction using the tresyl chloride method to couple an RGD-containing peptide to hyaluronate polymer.

The biodegradable polymer component of the present invention is hyaluronate, also known as hyaluronic acid (HA). HA consists of alternating residues of D-glucuronic acid and N-acetyl-D-glucosamine. This water soluble polymer is naturally found in nearly all tissue, especially in the extracellular matrix, the eyes and synovial fluid of joints. HA is commercially available in pure form. HA in the present invention generally has a molecular weight of 150,000 or greater, and more preferably 1 million or greater. Accordingly, the variable "n" in the HA polymers of FIGS. 1 to 3 is 375 or greater.

Figure 4A:
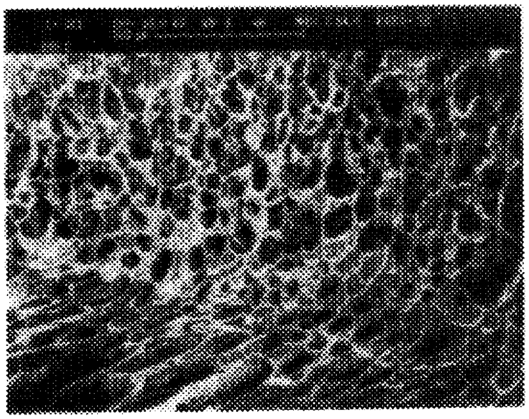
FIGS. 4A and 4B show the porous structure of a cross-linked hyaluronate RGD peptide scaffold.
Figure 4B:
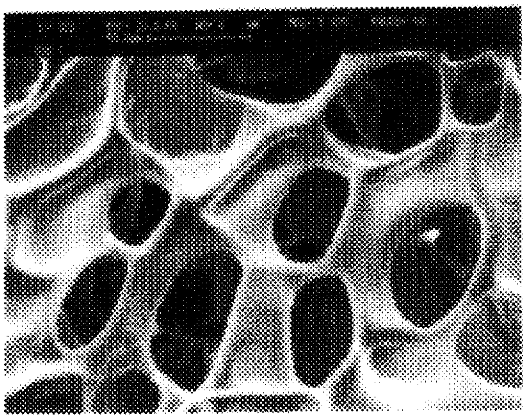

The HA polymer may be intermolecularly cross-linked to stabilize its physical properties. The present invention provides formation of stable cross-linked HA using multifunctional epoxides. As used herein, the term "multifunctional" epoxide means a chemical reagent having two or more epoxides present, such as lower aliphatic epoxides or their corresponding epiphalohydrins. Examples of multifunctional epoxides include, but are not limited to, the diepoxide 1,4 butanediol diglycidyl ether (BDDE), polyglycerolpolyglycidyl ether (PGPGE), pentaerythriolpolyglycidyl ether (PEPGE) and diglycerolpolyglycidyl ether (DGPGE). In a preferred embodiment, the diepoxide BDDE is used as the cross-linking agent. The sugar moieties of HA cross-link via the two epoxides of BDDE. As shown in FIG. 4 the resulting cross-linked HA is a porous material after lyophilization.

Cross-linked HA can be formulated into a variety of shapes, such as membranes, gels, sponges, or microspheres. The desired form and shape is achieved by employing the appropriate drying methods: air-drying leads to membranes, lyophilization produces sponge-like materials, while the product without drying is in gel form and takes the shape of its container. The viscosity of the semi-gel can be altered by the addition of unconjugated hyaluronate or varying the degree of peptide conjugate. The semi-gel can be placed directly in a wound to aid in healing by providing an artificial biodegradable matrix along with cell attachment, migration, and proliferation signals. In alternate embodiments the conjugate can be coated on a biodegradable mesh or other implanted material, or it can itself be formed into sheets or other structures, or can be maintained in a hydrated form.

Figure 5:
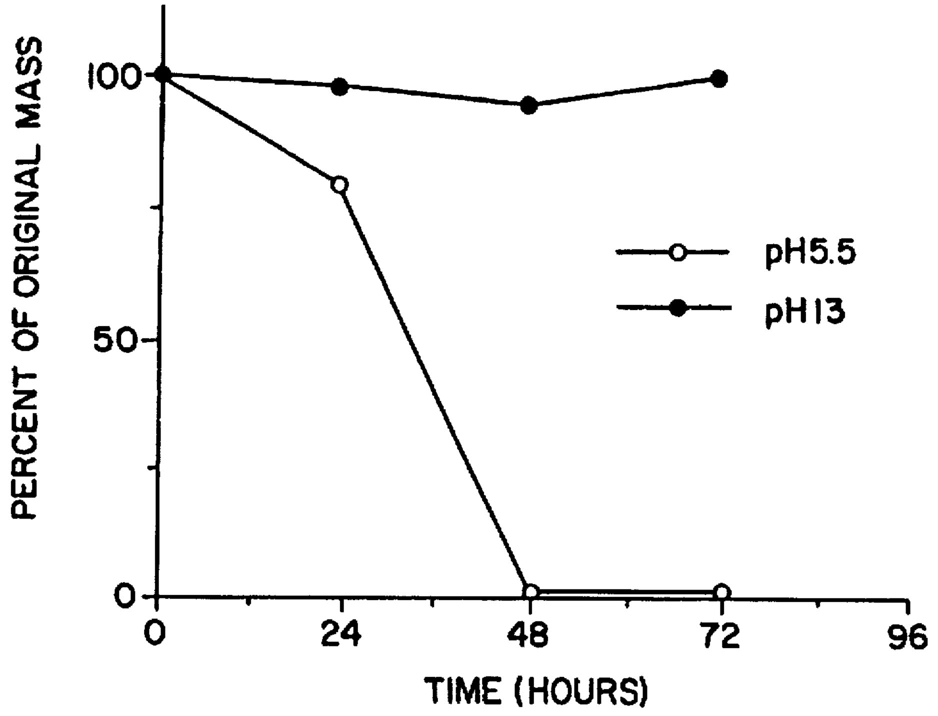
FIG. 5 diagrams the in vitro stability of hyaluronate cross-linked with BDDE at various pHs.

BDDE cross-linked HA can persist in dermal tissue anywhere from one to at least thirty days, depending on the amount of cross-linking. The variable residence time of the scaffold is created by the introduction of hydrolyzable bonds during the epoxide cross-linking. The materials cross-linked with epoxide at a lower pH have a greater amount of ester bond formation and therefore are more rapidly hydrolyzable. An example of the in vitro degradation of BDDE cross-linked HA is shown in FIG. 5.

Alternatively, or in addition thereto, the residence times can also be affected in the sodium periodate method depending on the number of reactive groups in the RGD-peptide which are available for attachment to HA. An example of a reactive group in the RGD-peptide which can attach to HA is a primary amine. A peptide containing two reactive groups, such as two primary amines, can itself cross-link the HA in the periodate method, thereby creating a more stable scaffold. On the other hand, where only one reactive group is present in the peptide, such as only one primary amine at the amino terminus, cross-linking HA through the peptide does not occur and a more biodegradable matrix results.

In addition to creating a cross-linked polymer with variable stability, the present invention also provides a variety of novel chemical methods to couple the active RGD-containing peptide to the HA polymer. The invention provides several coupling methods, including (1) an epoxide method, (2) a tresyl chloride method, and (3) a method using sodium periodate. The methods result in novel artificial matrices, having RGD-peptides immobilized to HA in new ways.

Prior art methods used to couple RGD peptides to HA are disclosed in a WO application and include the use of such coupling agents as 1-ethyl-3-3-dimethylaminopropylcarbodmiide (EDC), dicyclohexylcarbomide (DDC), glutaraldehyde, cyanogen bromide or N-hydroxysuccinimide. However, different forms of the scaffold are required for different tissue applications. Scaffolds prepared by the present invention have increased residence times and alternative forms, as described above and in the Examples. Scaffolds prepared by the present invention which can last up to thirty days are especially useful for indications where only one-time application is possible or in indications where multiple applications are not practical. The alternative residence time is due to the cross-linked HA. The coupling agents disclosed in the WO application, such as EDC and DDC, can generally serve as polymer cross-linkers provided certain reactive groups are present on the polymer. EDC, DDC, and the other coupling agents disclosed in the WO application, however, are incapable of cross-linking HA as provided by the present invention. U.S. Pat. No. 4,963,666 to Malson, which is incorporated herein by reference, discloses cross-linking HA with bi- or polyfunctional epoxides, such as BDDE. Malson does not, however, teach that the epoxide cross-linking agents can also be used for coupling RGD-containing peptides to HA.

The Epoxide Method

In one embodiment, the RGD peptide is immobilized to cross-linked hyaluronate using a multifunctional epoxide. For example, a bifunctional epoxide such as 1,4 butanediol diglycidyl ether (BDDE) can be used. Thus, BDDE can serve as both a cross-linking and a coupling agent and the invention has the advantage of using one reagent in a single reaction pot to accomplish all the chemistries. Examples of other multifunctional epoxides include, but are not limited to, polyglycerolpolyglycidyl ether (PGPGE), pentaerythriolpolyglycidyl ether (PEPGE) and diglycerolpolyglycidyl ether (DGPGE).

In the first step, the epoxide, such as BDDE, is added to an HA solution in excess and the reaction is allowed to proceed. Epoxides can react with from one to four of the hydroxyl groups on the sugar rings to form one to four ether linkages. Alternatively, or in addition to reacting with the hydroxyl groups, the epoxide can react with the carboxylic acid of the polysaccharide to form an ester bond. Where both epoxides of BDDE have reacted with the functional groups in the sugar rings of HA, the HA becomes cross-linked. Where only one epoxide has reacted with HA there remains a free epoxide attached to the sugar ring available for peptide coupling. After removing any excess BDDE from the reaction solution, an RGD-containing peptide is added to the solution and covalently coupled to the polysaccharide through the hydrophilic spacer arm between the peptide and sugar ring. An example of the peptide coupling by the epoxide method is provided in FIG. 2.

Tresyl Chloride Method

An alternative embodiment of the invention is preparing the peptide-polymer conjugates using a tresyl chloride method. This method involves, first activating the matrix with tresyl chloride, chemically known as 2,2,2-trifluoroethanesulfonyl chloride, followed by peptide coupling. In the first step, tresyl chloride is added drop-wise to a pyridine/acetone solution that contains HA matrix. The tresyl chloride is reactive with all four of the hydroxyl groups on the sugar rings, one of which is exemplified in FIG. 3. After the HA-tresylate is washed, in the second step, RGD peptide is coupled as indicated, for example, in FIG. 3.

In the tresyl chloride method, the peptide may be coupled directly to HA or via a linear spacer arm, such as for example, the spacer molecule 6-amino-1-hexanol. The spacer arm is first coupled to the HA matrix via tresyl activation and coupling steps. For coupling an RGD peptide to the spacer arm, the tresyl activation and coupling steps are repeated. Alternative spacer arms may be used, so long as they have characteristics similar to those of 6-amino-1-hexanol, namely a primary amine for coupling to the HA-tresylate, a reactive moiety, such as a hydroxyl group, for activation and coupling of RGD peptide, and a linear chain.

Unlike BDDE and the other multifunctional epoxides, which serve as both the cross-linking and coupling agent, tresyl chloride does not cross-link HA. The HA matrix used in the tresyl chloride method may, however, be cross-linked for additional stability. The cross-linking can be effected, for example, by using a multifunctional epoxide, such as BDDE, as described above. Cross-linking can be done either before or after peptide coupling.

The tresyl chloride method has advantages over other immobilization methods, including efficient coupling under very mild conditions, no side reactions during activation and coupling, and the RGD peptides can be bound directly to the carbon atoms of the HA support.

Sodium Periodate Method

Also provided by the present invention is a method of preparing the peptide-polymer conjugates using sodium periodate and sodium cyanoborohydride. Sodium periodate oxidizes one or both of the vicinal hydroxy groups in the glucuronic acid sugar ring to create one or two reactive aldehyde moieties in the sugar backbone which are then available for peptide immobilization. Surprisingly and unexpectedly by the instant invention, sodium periodate oxidizes trans-diols of glucuronic acid at a reasonable kinetic rate. An example of the aldehyde formation is provided in FIG. 1.

After periodate oxidation, peptide and sodium cyanoborohydride ($NaCNBH_3$) are added, either together or in sequential steps, respectively. The peptide reacts with either one or both of the aldehyde groups to immobilize RGD-peptides to HA. The sodium cyanoborohydride reduces the secondary imine formed between the peptide and sugar ring to a more stable secondary amine as exemplified in FIG. 1.

The HA may be cross-linked for additional stability. The cross-linking can be effected, for example, by using the cross-linking agent BDDE, or other multifunctional epoxides, either before or after peptide coupling.

Peptides conjugated to hyaluronate by the present invention contain the sequence Arg-Gly-Asp or D-Arg-Gly-Asp and have cell attachment promoting activity. Peptides containing the Arg-Gly-Asp and D-Arg-Gly-Asp sequence are capable of promoting cell attachment when they are presented on a matrix or on an insoluble substrate. When present in solution, RGD peptides inhibit cell attachment to RGD-containing adhesive proteins such as fibronectin.

As used herein, the terms "Arg-Gly-Asp peptide," "RGD peptide," "Arg-Gly-Asp-containing," or RGD-containing" refer to a peptide having at least one Arg-Gly-Asp-containing sequence which has cell attachment promoting activity. A peptide "containing the amino acid sequence "Y-Gly-Asp, wherein Y is Arg or D-Arg" also refers to a peptide having at least one Arg-Gly Asp-containing sequence which has cell attachment promoting activity. It is intended that the term "RGD peptide" in its broadest sense includes a peptide comprising Arg-Gly-Asp or a functional equivalent. For example, an amino acid such as lysine, ornithine, homoArginine (homoArg) or a mimic of these amino acids is a functional equivalent of arginine. Similarly mimics of Gly and Asp are functional equivalents of glycine and aspartic acid, respectively. Therefore, a peptide including, for example, Lys-Gly-Asp is considered an RGD peptide within the meaning of the present invention. As used herein, the term "mimic" means an amino acid or an amino acid analog that has the same or similar functional characteristic of an amino acid. Thus, for example, an arginine analog can be a mimic of arginine if the analog contains a side chain having a positive charge at physiological pH, as is characteristic of the guanidinium side chain reactive group of arginine. A peptide mimetic or peptidomimetic is an organic molecule that retains similar peptide chain pharmacophore groups as are present in the corresponding peptide. Peptide mimetics also can be functional equivalents of Arg-Gly-Asp. Moreover, the peptide can be linear or cyclic. The peptides may be cyclized by procedures well known in the art, such as through a disulfide bridge or through a lactam.

As used herein, the term "amino acid" in its broadest sense includes naturally occurring proteogenic amino acids and imino acids as well as non-naturally occurring amino acids and imino acids and analogs and mimics thereof. As used herein, the term "proteogenic" indicates that the amino acid can be incorporated into a protein in a cell through well-known metabolic pathways. In view of this broad definition of an amino acid, one of skill in the art would know that this definition includes, unless otherwise specifically indicated, naturally occurring proteogenic (L) amino acids, (D) amino acids, chemically modified amino acids including amino acid analogs, naturally occurring non-proteogenic amino acids such as norleucine and chemically synthesized compounds that have properties known in the art to be characteristic of an amino acid.

The following standard abbreviations are used herein to identify amino acid residues.

| Amino Acid | Three-letter Abbreviation | One-letter Symbol |
|---|---|---|
| Alanine | Ala | A |
| Arginine | Arg | R |
| D-Arginine | D-Arg | dR |

-continued

| Amino Acid | Three-letter Abbreviation | One-letter Symbol |
|---|---|---|
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| HomoArginine | HomoArg | |
| Isoleucine | Ile | I |
| Leucine | Leu | L |
| Lysine | Lys | K |
| Methionine | Met | M |
| Ornithine | Orn | |
| Penicillamine | Pen | |
| Phenylalanine | Phe | F |
| Amino-β, β-penta-methylene-β-mercaptopropionic acid | Pmc | |
| Proline | Pro | P |
| Serine | Ser | S |
| Threonine | Thr | T |
| Tryptophan | Trp | W |
| Tyrosine | Tyr | Y |
| Valine | Val | V |

The RGD-containing peptides can be produced synthetically or recombinantly or derived from naturally occurring proteins, such as fibronectin or vitronectin. The peptides are preferably synthetic for relative ease of manufacture and to avoid unnecessary extraction from blood. Standard procedures for preparing synthetic peptides are well known in the art, as disclosed for example in M. Bodanszky, *Principles of Peptide Synthesis*, (Springer-Verlag, New York, 1984), M. Bodanszky, *Peptide Chemistry*, 1st & 2nd eds., (Springer-Verlag, New York, 1988 & 1993), and *Solid Phase Peptide Synthesis*, (available from Pierce Chemical Co.), all which are incorporated herein by reference. Because the peptides do not carry species-specific immunological determinants they can be used in both veterinary and human applications. These peptides are also much more stable than fibronectin or other larger molecules in solution. In particular, D-Arg confers protease resistance. As well, the peptides can be protected at either or both termini, for example, by an acetyl (Ac), at the amino terminus and an amide ($NH_2$) at the carboxy terminus.

The smaller size of the peptide allows many more peptides to be attached to a given volume of hyaluronate. The peptides are generally of a size 20 amino acid residues or less, and preferably 10 or less. Such peptides, beside the Arg-Gly-Asp sequence, contain at least two additional amino acids independently selected from the D or L forms of Arg, Lys, Orn, or HomoArg. Amino acids other than Arg, Lys, Orn, or homoArg which contain a side chain having a positive charge at physiological pH could also be used. Therefore, the peptides have a total of at least three positively charged amino acid residues; the arginine of the RGD sequence and at least two additional positively charged amino acids. The peptides preferably contain at least four positively charged residues total. The additional positively charged amino acids can be positioned at either the amino terminal side of the Arg-Gly-Asp sequence (downstream) or at the carboxy terminal side of the Arg-Gly-Asp sequence (upstream), and can be together or apart. The two or more, preferably three or more, additional positively charged amino acids are generally in sequence, though this is not a requirement. For example, a preferred peptide, G dR dR dR dR dR G G G dR G D S P A S S K (SEQ ID No. 1) contains six arginines and has a net of six positive charges. The positive charges may aid peptide coupling by allowing the peptides to get close to the negatively charged HA.

Modification of the amino terminus of the peptide would be expected to diminish the need for the positively charged amino acids. Such modified peptides, having the Arg-Gly-Asp sequence and less than four total positive residues would be expected to conjugate with HA and support cell attachment. Addition of a strong nucleophile to the amino terminus of an Arg-Gly-Asp-peptide is one such means of manipulation.

In the preferred embodiments of the invention, the linear polypeptides that are useful in combination with hyaluronate to promote wound healing include the following:

Epoxide Method:

G dR dR dR dR dR G G G dR G D S P A S S K (SEQ ID No. 1);
G R R R R R G R G D I P $T_{NH2}$ (SEQ ID No. 2);
G R R R R R G G R G D I P $T_{NH2}$ (SEQ ID No. 3);
G R R R R G G G R G D I P $T_{NH2}$ (SEQ ID No. 4);
Ac G dR dR dR dR dR G G G dR G D S P A S S K (SEQ ID No. 5);
Ac R R R G G R G D I P $K_{NH2}$ (SEQ ID No. 6);
G R R R G G R G D I $P_{NH2}$ (SEQ ID No. 7);
G R R R G G G R G D I P $T_{NH2}$ (SEQ ID No. 8);
G R R R G G R G D I P $T_{NH2}$ (SEQ ID No. 9);
R R R R G R G D I P $T_{NH2}$ (SEQ ID No. 10);
R R R G R G D I P $T_{NH2}$ (SEQ ID No. 11); and
Ac G dR dR dR dR dR G G G dR G D S P A S S $K_{NH2}$ (SEQ ID No. 17);

Tresyl Chloride Method:

G dR dR dR dR dR G G G dR G D S P A S S K (SEQ ID No. 1);
G R R R R R G G G R G D I $P_{NH2}$ (SEQ ID No. 12);
Ac G R R R R R G G G R G D I P $K_{NH2}$ (SEQ ID No. 13);
G R R R R R G R G D I P $T_{NH2}$ (SEQ ID No. 2);
G R R R R R G G R G D I P $T_{NH2}$ (SEQ ID No. 3);
G R R R R G G G R G D I P $T_{NH2}$ (SEQ ID No. 4);
Ac G dR dR dR dR dR G G G dR G D S P A S S K (SEQ ID No. 5);
Ac R R R G G R G D I P $K_{NH2}$ (SEQ ID No. 6);
G R R R G G R G D I $P_{NH2}$ (SEQ ID No. 7);
G R R R G G G R G D I P $T_{NH2}$ (SEQ ID No. 8);
G R R R G G R G D I P $T_{NH2}$ (SEQ ID No. 9);
Ac R R G R G D I P $K_{NH2}$ (SEQ ID No. 14); and
Ac G dR dR dR dR dR G G G dR G D S P A S S $K_{NH2}$ (SEQ ID No. 17)

Sodium Periodate Method:

G dR dR dR dR dR G G G dR G D S P A S S K (SEQ ID No. 1);
G R G D S P A S S K K K K (SEQ ID No. 15);
R R R R R G D S P K (SEQ ID No. 16);
Ac G dR dR dR dR dR G G G dR G D S P A S S K (SEQ ID No.5);
G R R R R R G G G R G D I $P_{NH2}$ (SEQ ID No. 12);
G R R R R G G G R G D I P $T_{NH2}$ (SEQ ID No. 4)
G R R R R R G R G D I P $T_{NH2}$ (SEQ ID No. 2);
G R R R R R G G R G D I P $T_{NH2}$ (SEQ ID No. 3);
Ac G R R R R R G G G R G D I P $K_{NH2}$ (SEQ ID No. 13);
Ac G dR dR dR dR dR G G G dR G D S P A S S $K_{NH2}$ (SEQ ID No. 17);
G R R G R R G R G D I P $T_{NH2}$ (SEQ ID No. 18);
G R R G R R G R G D $T_{NH2}$ (SEQ ID No. 19);
R R R R G R G D I P $T_{NH2}$ (SEQ ID No. 10);
G R R G R R G R G D I $T_{NH2}$ (SEQ ID No. 20); and
R R G R R G R G D I P $T_{NH2}$ (SEQ ID No. 21).

In addition to the above linear peptides, cyclic RGD-containing peptides may also be used. The peptides may be cyclized by procedures well known in the art, such as through a disulfide bridge or through a lactam. Preferred cyclic disulfide peptides coupled to HA by any one of the methods of the present invention include the following:

K (Pen) G F R G D T P C R (SEQ ID No. 22);

-continued

R (Pmc) G H R G D R R C R (SEQ ID No. 23);

R (Pen) H R G D W R C R (SEQ ID No. 24);

R (Pen) P R G D W R C R (SEQ ID No. 25);

G (Pen) A A R G D N P C A (SEQ ID No. 26);

G (Pen) R A R G D N R C A (SEQ ID No. 27);

G (Pen) F R G D F C A K (SEQ ID No. 28);

G (Pen) R A R G D N P C A K (SEQ ID No. 29);

G dR dR dR dR dR G G G (Pen) F R G D S F C A S S K (SEQ ID No. 30);

and

R (Pen) F R G D T P C K (SEQ ID No. 31).

The present invention also provides a method of promoting wound healing by applying the compositions prepared by any one of the methods of the present invention. Compositions in the form of matrices or semi-gels prepared by the present invention are easily applied to wound areas. The semi-gel or other forms of matrices can be placed directly on the wound at the site or sites of matrix destruction. The wound is otherwise treated in a normal manner. For example, a semi-gel can be applied to dermal wounds such as chronic ulcer wounds resulting from various disease conditions such as diabetes or sickle-cell anemia which result in slower than normal wound healing. The semi-gel containing the RGD peptide is applied topically to the wound, and the ulcer covered with a gauze dressing.

As a semi-gel, the conjugate does not tend to migrate away from the wound site, either due to physical effects such as movement by the patient or by absorption by the patient's own system. The conjugate acts as a temporary replacement matrix that encourages cell migration into the wound and speeds healing. As the wound heals, the conjugate is slowly broken down by the migrating cells and replaced by natural replacement matrix.

Various RGD-peptide-hyaluronic acid scaffolds made by the described procedures can be tested in commonly used in vitro models for cell attachment and cell motility, as well as by in vivo dermal wound healing models such as those described for the RGD polymer conjugates described in patent application U.S. Ser. No. 08/176,999, now abandoned, which is herein incorporated by reference. Such compositions can be used on any wounds which involve body tissues being cut, abraded or otherwise damaged. Such wounds include chronic skin ulcers, including decubitus ulcers and diabetic ulcers, burns, corneal wounds, skin-graft donor sites, keloid-forming wounds, and incisions.

Additional in vivo animal models useful for testing compositions of the present invention include subcutaneous implantation of the composition in guinea pigs (Polarek et al., *Wounds* 6(2):46 (1994), Buckley et al., *PNAS USA* 82:7340 (1985)); rat incisional models (Shah et al., *Lancet*, 339:213 (1992)); rabbit ear ulcer model (Pierce et al., *Amer. J. Path.*, 138: 629–646 (1991)); rabbit knee femoral medial condyl defect (Von Shroeder et al., *J. Biomed. Mater. Res.* 25:329 (1991)); full thickness wounds in guinea pigs (Cheng et al., *Arch. Dermatol.* 124:221–226 (1988)); full thickness wounds in pigs (Welch et al., *J. Cell Biol.* 110:133–145 (1990)); and pig burn model (Davis et al., *J. Surg. Res.* 48:245–248 (1990)), all of which are herein incorporated by reference. Those of skill understand that the results of such in vivo experiments are analyzed for enhanced tissue deposition, rate of epithelialization, cell type reactivity, and growth factor delivery.

In addition, a method of promoting tissue regeneration is provided by the present invention by applying the compositions of the present invention in a manner described above. Regeneration of tissue such as cartilage, bone, or nervous tissue can be enhanced by applying the compositions of the present invention.

The compositions of the present invention are also useful as matrices to support cell growth and tissue regeneration in vitro. The RGD peptide-containing matrix can be used to coat surfaces to support and enhance primary and secondary tissue cultures, for example.

The peptide compositions of the present invention are useful in and of themselves when not conjugated to HA For instance, when present in solution, the peptides bind integrin-type receptors expressed on cell surfaces, and thereby prevent the cells from binding to natural molecules containing the Arg-Gly-Asp sequence, such as fibronectin and fibrinogen. Compositions that can prevent such binding are useful treatments in pathologies that depend on cell-cell interactions or cell-matrix interactions, such as cancer, osteoporosis, thrombosis, and the like. The present peptides also can be used to detach cells from in vitro culture vessels, when cells are attached to matrix proteins coating the vessel bottom or wall. The peptides provided by the present invention can also be used to promote cell attachment to a substrate when they are coated onto the substrate. Thus, coating a cell culture vessel or a prosthetic device with peptides of the present invention promotes attachment of cells to the vessel or device. Methods of using Arg-Gly-Asp peptides to inhibit or promote cell attachment are generally well known, and are described, for example, in U.S. Pat. Nos. 4,792,525, 4,879,237, 4,988,621, and 5,120,829.

The following examples are intended to illustrate but not limit the present invention.

EXAMPLE I

Peptide Synthesis

This example demonstrates the standard procedure used for preparing a synthetic RGD peptide.

The peptide G dR dR dR dR dR G G G dR G D S P A S S K (SEQ ID No. 1) was synthesized using an automated peptide synthesizer (Model 430A; Applied Biosystems, Foster City, Calif.) according to the directions provided by the manufacturer. After cleavage from the resin with hydrogen fluoride, the peptides were washed in cold ethyl ether and precipitated from solution in trifluoroacetate with ice cold ether. The peptides were then redissolved in distilled water and lyophilized. The peptides were further purified by HPLC using a Waters BONDAPAK™ $C_{18}$ (3×30 cm; 10 μm packing, Waters Assoc., Milford, Mass.). Other peptides can be made by the same method.

EXAMPLE II

Epoxide Method

This Example provides the preparation of RGD-peptide-polymer conjugates using a bifunctional epoxide as the cross-linking/coupling agent.

Cross-linking HA

Sodium hyaluronate, (12 mg) (Genzyme, Inc., Cambridge, Mass.) was dissolved in 1.0 ml of sodium carbonate ($Na_2CO_3$) solution (0.01M, pH 10). 150 µl of 1,4 butanediol diglycidyl ether (BDDE, 95%, Fuka Chemical, Ronkonkoma, N.Y.) was then added to the HA solution, followed by shaking at room temperature for 18–24 hours. Thereafter, the pH was adjusted to 7 by adding hydrochloric acid (HCl) solution and the solution diluted to a final volume of 3 ml using distilled water. The diluted HA solution was then placed in a concentrator tube (CentiPrep-3, molecular weight cut off (MWCO) of 10,000 to 12,000 daltons, Amicon, Inc., Beverly, Mass.) and centrifuged at 20°–25° C. at 3400 rpm until the final volume reached 1 ml. The pH of the concentrated HA solution to was adjusted to between 9 and 10.

Peptide Coupling 4.0 mg of pure peptide SEQ ID No. 1 as prepared by Example I was dissolved in 100 µl of $Na_2CO_3$ solution (0.01M, pH 10) and adjusted to a pH between 9 and 10 by adding a small volume of NaOH solution. The peptide solution was mixed with 0.9 ml of the BDDE-modified HA solution (peptide: HA was about 35:100, W:H) and shaken at room temperature for 24 hours.

Uncoupled peptide was removed by dialysis by adjusting the solution pH to 7 and dialyzing the solution with 2,000 ml of distilled water for 4 hours using cellulose ester dialysis membrane (Spectra/Por; Spectrum Medical Industries, Inc., Los Angeles, Calif., MWCO of 12,000 to 14,000 daltons). The solution was then loaded into the wells of a multiple-wells cell culture plate, degassed, and lyophilized at about −50° C.

Typical coupling concentrations of peptide are between 50–150 nmoles/mg HA, which is about 15% of peptide covalently bound.

EXAMPLE III

Tresyl Chloride Method

This Example details the preparation of an RGD-peptide-polymer conjugate using tresyl chloride.

Cross-Linked HA Matrix Preparation 10 mg of HA was dissolved in 1 ml of distilled water (pH 6), 10 µl of BDDE added, and the solution shaken at room temperature for 24 hours. The solution containing cross-linked HA was dialyzed against 2 L of distilled water for 32 hour using a semi-permeable membrane tube (MWCO of 12,000 to 14,000 daltons), followed by loading onto a 12 well cell-culture plate (0.75 ml per well), degassing and lyophilization. The resulting porous materials was punched into a round piece with the diameter of 4–6 mm. The HA matrix was predried by placing the cross-linked HA in dry acetone (pre-dried with molecular sieve) for at least one day.

Activation Step

The dried, cross-linked HA matrix was placed in 2 ml of dry pyridine containing 100 µl of dry acetone. One gram of tresyl chloride was drop-wise added to the pyridine/HA mixture for one minute under shaking. The matrix was then washed with acid acetone solutions in the sequence of 8/2, 5/5, 2/8, and 0/10 (acetone/1 mM HCl, v/v), then 0.2M $NaHCO_3$ briefly.

Peptide Coupling

The activated HA-tresylate was placed in a peptide solution (10 mg/ml pure peptide of SEQ ID No. 1 in 0.2M $NaHCO_3$, pH 8) and shaken at room temperature for 4 hr. The solution was washed with high-salt/low-pH (1% acetic acid/1M NaCl) solution until no blue color was detected in the washing solution using ninhydrin reagent as an indicator. Thereafter the solution was washed with distilled water and lyophilized.

This method also can be used to couple peptides to soluble HA followed by cross-linking with BDDE. Coupling usually yields between 10–50 nmoles peptide/mg HA, which is about 4% of peptide covalently bound.

EXAMPLE IV

Sodium Periodate Method

This Example illustrates the use of sodium periodate to prepare RGD-peptide-HA-polymer conjugates.

Reaction solution (1 ml) was prepared as follows. Sodium periodate (prepared fresh in Milli Q water with stock solutions ranging from 100–500 mM) was diluted into sodium acetate buffer (100 mM, pH 5.6) to the desired concentration of 0.1–75 mM. Sodium Cyanoborohydride ($NaCNBH_3$) (1–1.5M stock made up in Milli Q water used within one hour and made fresh each time) at final concentration of 50 mM, and peptides at a concentration of greater than 0.5 mg/ml was added to the sodium periodate solution.

One to two milligrams of cross-linked HA (cross-linked using BDDE as described above) was added to the sodium periodate/NaCNBH peptide solution and incubated at room temperature for at least 2 hours on a rocker. Degassing was used where air was trapped inside the matrices. The matrices were washed 3 to 5 times with Milli Q water to remove unreactive components followed by a five minute wash at room temperature with low pH/high salt buyer (1% acetic acid/1M NaCl) and then water washing and lyophilization.

This method also can be used to couple peptides to soluble HA followed by cross-linking with BDDE. Coupling yields approximately 75–200 nmoles peptide per mg. HA.

EXAMPLE V

Standard Cell Attachment

The conjugates prepared by the above described methods, as well as conjugates containing other RGD-peptide sequences, were tested for cell attachment using the following procedures.

Pre-Assay Set Up

New subcultures are made the day before the assay and allowed to grow to 75–80% confluency. When a 100×20 mm dish was 80–90% confluent the cells were detached by adding 4 ml of trypsin/EDTA. When the cells become rounded they are suspended by adding 6 ml of complete media to the 4 ml of trypsin/EDTA (10 ml total). Forty to fifty percent of the cell suspensions were transferred to a new 100×20 mm dish and cultured as usual. One 100×20 mm dish is sufficient to perform 6 cell attachments.

Cell attachment assay

Samples to be tested are placed in 0.5 ml blocking solution (HBSS, 3% BSA, 25 mM Hepes pH 7.0) until needed. Each 100×20 mm dish was trypsinized using 4 ml of trypsin/EDTA for approximately 10 minutes or until cells were easily detached. Cells should not be detached too soon or they will remain aggregated during the cell attachment assay. It is desirable to obtain a good single cell suspension. If clumps of cells are observed let them settle out before using and adjust for the loss of cells in the assay.

The cells were detached from the plate using 6 ml of serum free media (SFM) supplemented with ITS+ (Insulin Transferrin Selenium (Collaborative Research, Inc., Bedford, Mass.), SFM+ITS+=SFM+) for a total volume of 10 ml (4 ml of trypsin/EDTA+6 ml of SFM+). The cells were centrifuged one time to pellet the cells and then they were resuspended in 5 ml of soybean trypsin inhibitor (SBTI) diluted in SFM+. The cells were incubated in SBTI/SFM+ for 10 minutes in a 37° C. water bath. While trypsin was being inactivated, the blocking buyer was removed and the samples suspended in 1 ml of SFM+.

Cells were centrifuged 1 time to remove SBTI. Resuspended cells in 6 ml of SFM+ created a good single cell suspension. If necessary, the resuspended cells can sit on the bench for 5 minutes to let aggregates settle to the bottom before applying to the matrices. Approximately 1 ml of cell suspension per matrix (1–2 mg) was used. The matrix/cells were placed on a rocker in the incubator and cell attachment allowed to go for one to one and half hours. Thereafter, samples were transferred to a 12 well dish and washed 2 times with PBS using an orbital shaker. Neutral red solution (diluted 1:100) was added to PBS and incubated with the cells for 20 minutes on an orbital shaker. Two mls of stain/fix (PBS, 8% formaldehyde, crystal violet 0.0008%) was added and staining allowed to proceed for 2 hours at room temperature on the orbital shaker. Formaldehyde solution was removed and distilled water added. Cell attachment was assessed by microscopy.

All conjugates showed peptide-dependent cell attachment; there was little or no cell attachment to the HA alone but significant cell attachment to the peptide-HA conjugates. The results of testing several RGD-peptide-HA conjugates prepared by the three methods of the invention are presented in Table 1.

buyer (coating buffer) for five hours at room temperature. Coverslips were then washed with PBS and seeded with MG63 human osteosarcoma cells at 60% coniluency. Attachment usually takes between three and four hours.

Figure 6:
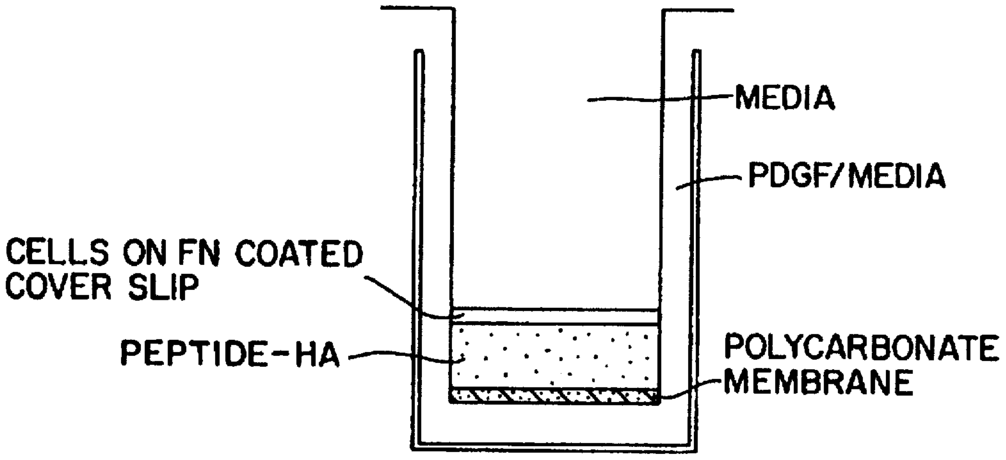
FIG. 6 diagrams the components used in the inverted disk cell motility assay.

After attachment, the coverslips were washed with serum free Dulbecco's modified Eagle's medium (DMEM) containing ITS+. The coverslip was inverted onto a SEQ ID No.1-HA conjugate prepared by the above sodium periodate method or SEQ ID No.19-HA conjugates prepared by the BDDE and tresyl methods, as well as a control as diagrammed in FIG. 6. The motility assay was carried out for fifteen hours at 37° C. and 7% carbon dioxide, done entirely in the serum free medium, ITS+. The concentration of platelet derived growth factor (PDGF) in the outer chamber was 40 ng/ml. The following day cells were visualized using the standard neutral red/crystal violet method of staining.

In all cases, cells migrated on the peptide-modified HA, but not on the control HA lacking peptide.

Using the same method as described above, the effects of varying concentrations of HA on cell motility was also examined for 7.5, 10, and 15 mg/ml of HA.

Cells migrated at all HA concentrations tested, indicating that the HA-peptide conjugates exhibited mechanical stability sufficient to support cell migration.

EXAMPLE VII

Full Thickness Wounds In Guinea Pigs

Following the procedures for the full thickness wound model in guinea pigs described in Cheng et al., Arch.

TABLE 1

CELL ATTACHMENT ASSAY RESULTS

| SEQUENCE | SEQ. ID. NO. | SODIUM PERIODATE | TRESYL CHLORIDE | BDDE |
|---|---|---|---|---|
| GdRdRdRdRGGGdRGDSPASSK | 1 | + | + | + |
| GRRRRRGGGRGDIP$_{NH2}$ | 12 | + | + | NT |
| AcGRRRRRGGGRGDIPK$_{NH2}$ | 13 | + | + | NT |
| GRRRRRGGRGDIPT$_{NH2}$ | 2 | + | + | + |
| GRRRRGGGRGDIPT$_{NH2}$ | 3 | + | + | + |
| GRRRRGGGRGDIPT$_{NH2}$ | 4 | + | + | + |
| GRRGRRGRGDIPT$_{NH2}$ | 18 | + | NT | – |
| AcGdRdRdRdRdRGGGdRGDSPASSK | 5 | + | NT | + |
| AcRRRGGRGDIPK$_{NH2}$ | 6 | – | + | + |
| GRRRGGRGDIP$_{NH2}$ | 7 | – | + | + |
| GRRRGGGRGDIPT$_{NH2}$ | 8 | – | + | + |
| GRRRGGRGDIPT$_{NH2}$ | 9 | – | + | + |
| RRRRGRGDIPT$_{NH2}$ | 10 | + | NT | + |
| RRRGRGDIPT$_{NH2}$ | 11 | NT | NT | + |
| AcRRGRGDIPK$_{NH2}$ | 14 | – | + | N |

+ = positive cell attachment
– = no cell attachment
NT = not tested

In addition to the data provided in Table I relating to cell attachment of linear RGD-peptides coupled to HA by the various methods, all of the cyclic RGD-peptides described above at page 17 were coupled to HA using the sodium periodate method and tested for cell attachment. All conjugates showed positive cell attachment which was peptide-dependent.

EXAMPLE VI

Inverted Disk Cell Motility Assay

Plastic coverslips were coated with human plasma fibronectin (FN) at 10 µg/ml in 0.2M sodium carbonate Dermatol. 124:221–226 (1988), which is incorporated herein by reference, various peptide-HA conjugates prepared by the above-described methods were analyzed.

In all cases, fibroblast ingrowth into the HA matrices was seen in guinea pig full thickness wound models at approximately 4–5 days. Further, there was no inflammatory reaction to the and angiogenesis occurred throughout each material. All the cell ingrowth was peptide dependent and non-peptide modified materials were excluded from the wound bed.

Residence Times

The residence times were determined by Alcian staining and were as follows:

Epoxide Method

Two peptide-HA matrices, one with a peptide corresponding to SEQ ID No. 1, the other with a peptide having the sequence of SEQ ID No. 5, were prepared by the BDDE procedure described. Both matrices were stable in the wound bed for approximately 7–10 days.

Tresyl Chloride Method

BDDE cross-linked HA created at pH 6 and coupled to peptides corresponding to SEQ ID Nos. 1 or 5 by the tresyl chloride method described were present in the dermal wound for approximately 10–14 days.

Sodium Periodate Method

Sample peptides having only one primary amine, including SEQ ID Nos. 5, 12, and 19, each conjugated to HA by the described periodate method had residence times of 7–10 days before there is no detectable material by Alcian staining. Sample peptide having two amines, SEQ ID No. 1, conjugated to HA via sodium periodate was stable for at least 30 days.

Various Forms Tested

Porous powdered material created by the sodium periodate method was integrated into the wound bed and behaved in a similar manner to that of sponge-like forms. The thin film of material is non-porous and essentially solid. Because of its solid nature cells only grow on the surface or around the thin film of material. Therefore, the thin film geometry is not suitable for cell ingrowth and the material was moved out of the wound by cell infiltration.

Although the invention has been described with reference to the examples provided above, it should be understood that various modifications can be made by those skilled in the art without departing from the invention. Accordingly, the invention is set out in the following claims.

We claim:

1. A composition comprising cross-linked hyaluronate (HA) polymer and a peptide having cell attachment promoting activity containing the amino acid sequence Y-Gly-Asp, wherein Y is Arg or D-Arg, said peptide further containing at least two additional amino acids independently selected from the group consisting of Arg, D-Arg, Lys, D-Lys, Orn, D-Orn, L-HomoArg, and D-HomoArg, wherein said HA and said peptide are coupled with a multifunctional epoxide linked to the sugar backbone of HA.

2. The composition of claim 1, wherein the multifunctional epoxide is linked to HA via at least one ether bond.

3. The composition of claim 2, wherein the multifunctional epoxide is linked to HA via more than one ether bond.

4. The composition of claim 1, wherein the multifunctional epoxide is linked to HA via an ester bond.

5. The composition of claim 1, wherein the multifunctional epoxide is linked to HA via at least one ether bond and an ester bond.

6. The composition of claim 1, wherein the multifunctional epoxide is selected from the group consisting of butanediol diglycidyl ether (BDDE), polyglycerolpolyglycidyl ether (PGPGE), pentaerythriolpolyglycidyl ether (PEPGE) and diglycerolpolyglycidyl ether (DGPGE).

7. The composition of claim 6, wherein the multifunctional epoxide is BDDE.

8. The composition of claim 1, wherein said peptide contains at least three additional amino acids independently selected from the group consisting of Arg, D-Arg, Lys, D-Lys, Orn, D-Orn, L-HomoArg, and D-HomoArg.

9. The composition of claim 1, wherein at least two of said additional amino acids are in sequence.

10. The composition of claim 1 wherein the size of said peptide is equal to or less than 10 amino acid residues.

11. The composition of claim 1, wherein said peptide is selected from the group consisting of:

G R R R R R G R G D I P $T_{NH2}$ (SEQ ID No. 2);
G R R R R R G G R G D I P $T_{NH2}$ (SEQ ID No. 3);
G R R R R G G G R G D I P $T_{NH2}$ (SEQ ID No. 4);
Ac R R R G G R G D I P $K_{NH2}$ (SEQ ID No. 6);
G R R R G G R G D I $P_{NH2}$ (SEQ ID NO. 7);
G R R R G G G R G D I P $T_{NH2}$ (SEQ ID No. 8);
G R R R G G R G D I P $T_{NH2}$ (SEQ ID No. 9);
R R R R G R G D I P $T_{NH2}$ (SEQ ID NO. 10);
R R R G R G D I P $T_{NH2}$ (SEQ ID NO. 11); and
polypeptides containing any of the above sequences.

12. A method for preparing cross-linked HA polymer and a peptide having cell attachment promoting activity containing the amino acid sequence Y-Gly-Asp, wherein Y is Arg or D-Arg, said peptide further containing at least two additional amino acids independently selected from the group consisting of Arg, D-Arg, Lys, D-Lys, Orn, D-Orn, L-HomoArg, and D-HomoArg, comprising reacting a solution of HA with a multifunctional epoxide in the presence of said peptide so as to simultaneously cross-link HA and couple said peptide to said HA.

13. The method of claim 12, wherein the multifunctional epoxide is BDDE.

14. A composition produced by the method of claim 12.

15. A method of treating a wound, comprising placing the composition of claim 1 into a wound.

16. The method of claim 15, wherein said wound is selected from the group consisting of a severe burn, a skin graft donor site, a decubitus ulcer, a diabetic ulcer, a surgical incision, and a keloid-forming wound.

17. A method of inducing tissue regeneration comprising placing the composition of claim 1 on the area where said tissue regeneration is desired.

18. A composition comprising HA polymer and a peptide having cell attachment promoting activity containing the amino acid sequence Y-Gly-Asp, wherein Y is Arg or D-Arg, said peptide further containing at least two additional amino acids independently selected from the group consisting of Arg, D-Arg, Lys, D-Lys, Orn, D-Orn, L-HomoArg, and D-HomoArg, wherein said HA and said peptide are coupled with tresyl chloride and said peptide is linked to HA via more than one methylene bridge.

19. The composition of claim 18, wherein the HA polymer is cross-linked.

20. The composition of claim 18, further comprising a linear spacer arm between said HA polymer and said peptide.

21. The composition of claim 20, wherein the linear spacer arm is 6-amino-1-hexanol.

22. The composition of claim 18, wherein said peptide contains at least three additional amino acids independently selected from the group consisting of Arg, D-Arg, Lys, D-Lys, Orn, D-Orn, L-HomoArg, and D-HomoArg.

23. The composition of claim 18, wherein at least two of said additional amino acids are in sequence.

24. The composition of claim 18 wherein the size of said peptide is equal to or less than 10 amino acid residues.

25. The composition of claim 18, wherein said peptide is selected from the group consisting of:

G R R R R R G G G R G D I $P_{NH2}$ (SEQ ID No. 12);
Ac G R R R R R G G G R G D I P $K_{NH2}$ (SEQ ID No. 13);
G R R R R R G R G D I P $T_{NH2}$ (SEQ ID No. 2);
G R R R R R G G R G D I P $T_{NH2}$ (SEQ ID No. 3);
G R R R R G G G R G D I P $T_{NH2}$ (SEQ ID No. 4);
Ac R R R G G R G D I P $K_{NH2}$ (SEQ ID No. 6);
G R R R G G R G D I $P_{NH2}$ (SEQ ID No. 7);
G R R R G G G R G D I P $T_{NH2}$ (SEQ ID NO. 8);
G R R R G G R G D I P $T_{NH2}$ (SEQ ID No. 9);
Ac R R G R G D I P $K_{NH2}$ (SEQ ID No. 14); and
polypeptides containing any of the above sequences.

26. A method for preparing HA polymer coupled to a peptide having cell attachment promoting activity containing the amino acid sequence Y-Gly-Asp, wherein Y is Arg or D-Arg, said peptide further containing at least two additional amino acids independently selected from the group consisting of Arg, D-Arg, Lys, D-Lys, Orn, D-Orn, L-HomoArg, and D-HomoArg, comprising a. coupling a linear spacer arm to HA prior to coupling said peptide, said linear spacer arm having more than one methylene;

b. activating said HA with tresyl chloride to obtain tresylate-HA; and c. coupling the primary amine of the peptide with the tresylate-HA to couple the peptide on the HA, wherein the HA polymer and said peptide are linked via more than one methylene bridge.

27. The method of claim 26, further comprising cross-linking the HA with BDDE.

28. The method of claim 27, wherein the cross-linking step is done prior to activating HA with tresyl chloride.

29. The method of claim 26, wherein the linear spacer arm is 6-amino-1-hexanol.

30. A composition produced by the method of claim 26.

31. A method of treating a wound, comprising placing the composition of claim 18 into a wound.

32. The method of claim 31, wherein said wound is selected from the group consisting of a severe burn, a skin graft donor site, a decubitus ulcer, a diabetic ulcer, a surgical incision, and a keloid-forming wound.

33. A method of inducing tissue regeneration comprising placing the composition of claim 18 on the area where said tissue regeneration is desired.

34. A peptide having cell attachment activity comprising one of the following sequences:

G R R R R R G R G D I P $T_{NH2}$ (SEQ ID No. 2);

G R R R R R G G R G D I P $T_{NH2}$ (SEQ ID No. 3) ;

G R R R R G G G R G D I P $T_{NH2}$ (SEQ ID No. 4);

Ac R R R G G R G D I P $K_{NH2}$ (SEQ ID No. 6);

G R R R G G R G D I $P_{NH2}$ (SEQ ID No. 7);

G R R R G G G R G D I P $T_{NH2}$ (SEQ ID No. 8);

G R R R G G R G D I P $T_{NH2}$ (SEQ ID No. 9);

R R R R G R G D I P $T_{NH2}$ (SEQ ID No. 10);

R R R G R G D I P $T_{NH2}$ (SEQ ID No. 11);

G R R R R R G G G R G D I $P_{NH2}$ (SEQ ID No. 12);

Ac G R R R R R G G G R G D I P $K_{NH2}$ (SEQ ID No. 13);

Ac R R G R G D I P $K_{NH2}$ (SEQ ID No. 14);

G R G D S P A S S K K K K (SEQ ID No. 15);

G R R G R R G R G D I P $T_{NH2}$ (SEQ ID No. 18);

G R R G R R G R G D $T_{NH2}$ (SEQ ID No. 19);

G R R G R R G R G D I $T_{NH2}$ (SEQ ID No. 20); and

R R G R R G R G D I P $T_{NH2}$ (SEQ ID No. 21).

* * * * *

UNITED STATES PATENT AND TRADEMARK OFFICE

CERTIFICATE OF CORRECTION

PATENT NO. : 5,677,276
DATED : October 14, 1997
INVENTOR(S) : Dickerson et al.

It is certified that error appears in the above-identified patent and that said Letters Patent is hereby corrected as shown below:

Column 6,
Line 12, please delete "RGD-containing"" and replace therefor with -- RGD-containing" --.
Line 16, please delete ""containing" and replace therefor with -- containing --.

Column 10,
Line 23, please delete "HA For" and replace therefor with -- HA. For --.

Column 13,
Line 6, please delete "buyer" and replace therefor with -- buffer --.
TABLE 1, SEQUENCE column 1, line 1, please delete "GdRdRdRdRGGGdRGDSPASSK" and replace therefor with -- GdRdRdRdRdRGGGdRGDSPASSK --.
TABLE 1, SEQUENCE column 5, line 5, please delete "$GRRRRGGGRGDIPT_{NH2}$" and replace therefor with -- $GRRRRRGGRGDIPT_{NH2}$ --.

Column 14,
Line 1, please delete "buyer" and replace therefor with -- buffer --.

Signed and Sealed this

Twenty-first Day of August, 2001

Attest:

Nicholas P. Godici

NICHOLAS P. GODICI
Acting Director of the United States Patent and Trademark Office Attesting Officer

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 18 amino acids
( B ) TYPE: amino acid
( D ) TOPOLOGY: linear ( i x ) FEATURE:
( A ) NAME/KEY: Peptide
( B ) LOCATION: 2..6
( D ) OTHER INFORMATION: /note= "Xaa = D-Arginine (dR)"

( i x ) FEATURE:
( A ) NAME/KEY: Peptide
( B ) LOCATION: 10
( D ) OTHER INFORMATION: /note= "Xaa = D-Arginine (dR)"

( x i ) SEQUENCE DESCRIPTION: SEQ ID NO:1:

```
Gly Xaa Xaa Xaa Xaa Xaa Gly Gly Gly Xaa Gly Asp Ser Pro Ala Ser
1               5                   10                  15

Ser Lys
```

( 2 ) INFORMATION FOR SEQ ID NO:2:

( i ) SEQUENCE CHARACTERISTICS:
( A ) LENGTH: 13 amino acids
( B ) TYPE: amino acid
( D ) TOPOLOGY: linear ( i x ) FEATURE:
( A ) NAME/KEY: Modified-site
( B ) LOCATION: 13
( D ) OTHER INFORMATION: /note= "Peptide is amidated at the C- terminus."

( x i ) SEQUENCE DESCRIPTION: SEQ ID NO:2:

```
Gly Arg Arg Arg Arg Arg Gly Arg Gly Asp Ile Pro Thr
1               5                   10
```

( 2 ) INFORMATION FOR SEQ ID NO:3:

( i ) SEQUENCE CHARACTERISTICS:
( A ) LENGTH: 14 amino acids
( B ) TYPE: amino acid
( D ) TOPOLOGY: linear ( i x ) FEATURE:
( A ) NAME/KEY: Modified-site
( B ) LOCATION: 14
( D ) OTHER INFORMATION: /note= "Peptide is amidated at the C- terminus."

( x i ) SEQUENCE DESCRIPTION: SEQ ID NO:3:

Gly Arg Arg Arg Arg Arg Gly Gly Arg Gly Asp Ile Pro Thr
1 5 10

( 2 ) INFORMATION FOR SEQ ID NO:4:

( i ) SEQUENCE CHARACTERISTICS:
( A ) LENGTH: 14 amino acids
( B ) TYPE: amino acid
( D ) TOPOLOGY: linear ( i x ) FEATURE:
( A ) NAME/KEY: Modified-site
( B ) LOCATION: 14
( D ) OTHER INFORMATION: /note= "Peptide is amidated at C- terminus."

( x i ) SEQUENCE DESCRIPTION: SEQ ID NO:4:

Gly Arg Arg Arg Arg Gly Gly Gly Arg Gly Asp Ile Pro Thr
1 5 10

( 2 ) INFORMATION FOR SEQ ID NO:5:

( i ) SEQUENCE CHARACTERISTICS:
( A ) LENGTH: 18 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /note= "Peptide is acetylated at N- terminus."

( i x ) FEATURE:
( A ) NAME/KEY: Peptide
( B ) LOCATION: 2..6
( D ) OTHER INFORMATION: /note= "Xaa = D-Arginine (dR)"

( i x ) FEATURE:
( A ) NAME/KEY: Peptide
( B ) LOCATION: 10
( D ) OTHER INFORMATION: /note= "Xaa = D-Arginine (dR)"

( x i ) SEQUENCE DESCRIPTION: SEQ ID NO:5:

Gly Xaa Xaa Xaa Xaa Xaa Gly Gly Gly Xaa Gly Asp Ser Pro Ala Ser
1 5 10 15

Ser Lys ( 2 ) INFORMATION FOR SEQ ID NO:6:

( i ) SEQUENCE CHARACTERISTICS:
( A ) LENGTH: 11 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /note= "Peptide is acetylated at N- terminus."

( i x ) FEATURE:
( A ) NAME/KEY: Modified-site
( B ) LOCATION: 11
( D ) OTHER INFORMATION: /note= "Peptide is amidated at -continued C- terminus."

( x i ) SEQUENCE DESCRIPTION: SEQ ID NO:6:

Arg Arg Arg Gly Gly Arg Gly Asp Ile Pro Lys
1 5 10

( 2 ) INFORMATION FOR SEQ ID NO:7:

( i ) SEQUENCE CHARACTERISTICS:
( A ) LENGTH: 11 amino acids
( B ) TYPE: amino acid
( D ) TOPOLOGY: linear ( i x ) FEATURE:
( A ) NAME/KEY: Modified-site
( B ) LOCATION: 11
( D ) OTHER INFORMATION: /note= "Peptide is amidated at C- terminus."

( x i ) SEQUENCE DESCRIPTION: SEQ ID NO:7:

Gly Arg Arg Arg Gly Gly Arg Gly Asp Ile Pro
1 5 10

( 2 ) INFORMATION FOR SEQ ID NO:8:

( i ) SEQUENCE CHARACTERISTICS:
( A ) LENGTH: 13 amino acids
( B ) TYPE: amino acid
( D ) TOPOLOGY: linear ( i x ) FEATURE:
( A ) NAME/KEY: Modified-site
( B ) LOCATION: 13
( D ) OTHER INFORMATION: /note= "Peptide is amidated at C- terminus."

( x i ) SEQUENCE DESCRIPTION: SEQ ID NO:8:

Gly Arg Arg Arg Gly Gly Gly Arg Gly Asp Ile Pro Thr
1 5 10

( 2 ) INFORMATION FOR SEQ ID NO:9:

( i ) SEQUENCE CHARACTERISTICS:
( A ) LENGTH: 12 amino acids
( B ) TYPE: amino acid
( D ) TOPOLOGY: linear ( i x ) FEATURE:
( A ) NAME/KEY: Modified-site
( B ) LOCATION: 12
( D ) OTHER INFORMATION: /note= "Peptide is amidated at C- terminus."

( x i ) SEQUENCE DESCRIPTION: SEQ ID NO:9:

Gly Arg Arg Arg Gly Gly Arg Gly Asp Ile Pro Thr
1 5 10

( 2 ) INFORMATION FOR SEQ ID NO:10:

( i ) SEQUENCE CHARACTERISTICS:
( A ) LENGTH: 11 amino acids
( B ) TYPE: amino acid
( D ) TOPOLOGY: linear ( i x ) FEATURE:
( A ) NAME/KEY: Modified-site
( B ) LOCATION: 11
( D ) OTHER INFORMATION: /note= "Peptide is amidated at C- terminus."

( x i ) SEQUENCE DESCRIPTION: SEQ ID NO:10:

-continued

Arg Arg Arg Arg Gly Arg Gly Asp Ile Pro Thr
1 5 10

( 2 ) INFORMATION FOR SEQ ID NO:11:

( i ) SEQUENCE CHARACTERISTICS:
( A ) LENGTH: 10 amino acids
( B ) TYPE: amino acid
( D ) TOPOLOGY: linear ( i x ) FEATURE:
( A ) NAME/KEY: Modified-site
( B ) LOCATION: 10
( D ) OTHER INFORMATION: /note= "Peptide is amidated at C- terminus."

( x i ) SEQUENCE DESCRIPTION: SEQ ID NO:11:

Arg Arg Arg Gly Arg Gly Asp Ile Pro Thr
1 5 10

( 2 ) INFORMATION FOR SEQ ID NO:12:

( i ) SEQUENCE CHARACTERISTICS:
( A ) LENGTH: 14 amino acids
( B ) TYPE: amino acid
( D ) TOPOLOGY: linear ( i x ) FEATURE:
( A ) NAME/KEY: Modified-site
( B ) LOCATION: 14
( D ) OTHER INFORMATION: /note= "Peptide is amidated at C- terminus."

( x i ) SEQUENCE DESCRIPTION: SEQ ID NO:12:

Gly Arg Arg Arg Arg Arg Gly Gly Gly Arg Gly Asp Ile Pro
1 5 10

( 2 ) INFORMATION FOR SEQ ID NO:13:

( i ) SEQUENCE CHARACTERISTICS:
( A ) LENGTH: 15 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /note= "Peptide is acetylated at N- terminus."

( i x ) FEATURE:
( A ) NAME/KEY: Modified-site
( B ) LOCATION: 15
( D ) OTHER INFORMATION: /note= "Peptide is amidated at C- terminus."

( x i ) SEQUENCE DESCRIPTION: SEQ ID NO:13:

Gly Arg Arg Arg Arg Arg Gly Gly Gly Arg Gly Asp Ile Pro Lys
1 5 10 15

( 2 ) INFORMATION FOR SEQ ID NO:14:

( i ) SEQUENCE CHARACTERISTICS:
( A ) LENGTH: 9 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /note= "Peptide is acetylated at N- terminus."

( i x ) FEATURE:
( A ) NAME/KEY: Modified-site
( B ) LOCATION: 9
( D ) OTHER INFORMATION: /note= "Peptide is amidated at C- terminus."

( x i ) SEQUENCE DESCRIPTION: SEQ ID NO:14:

Arg Arg Gly Arg Gly Asp Ile Pro Lys
1 5

( 2 ) INFORMATION FOR SEQ ID NO:15:

( i ) SEQUENCE CHARACTERISTICS:
( A ) LENGTH: 13 amino acids
( B ) TYPE: amino acid
( D ) TOPOLOGY: linear ( x i ) SEQUENCE DESCRIPTION: SEQ ID NO:15:

Gly Arg Gly Asp Ser Pro Ala Ser Ser Lys Lys Lys Lys
1 5 10

( 2 ) INFORMATION FOR SEQ ID NO:16:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:16:

Arg Arg Arg Arg Arg Gly Asp Ser Pro Lys
1 5 10

( 2 ) INFORMATION FOR SEQ ID NO:17:

( i ) SEQUENCE CHARACTERISTICS:
( A ) LENGTH: 18 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /note= "Peptide is acetylated at N- terminus."

( i x ) FEATURE:
( A ) NAME/KEY: Peptide
( B ) LOCATION: 2..6
( D ) OTHER INFORMATION: /note= "Xaa = D-Arginine (dR)."

( i x ) FEATURE:
( A ) NAME/KEY: Peptide
( B ) LOCATION: 10
( D ) OTHER INFORMATION: /note= "Xaa = D-Arginine (dR)."

( i x ) FEATURE:
( A ) NAME/KEY: Modified-site
( B ) LOCATION: 18
( D ) OTHER INFORMATION: /note= "Peptide is amidated at C- terminus."

( x i ) SEQUENCE DESCRIPTION: SEQ ID NO:17:

Gly Xaa Xaa Xaa Xaa Xaa Gly Gly Gly Xaa Gly Asp Ser Pro Ala Ser
1 5 10 15

Ser Lys ( 2 ) INFORMATION FOR SEQ ID NO:18:

( i ) SEQUENCE CHARACTERISTICS:
( A ) LENGTH: 13 amino acids
( B ) TYPE: amino acid ( D ) TOPOLOGY: linear ( i x ) FEATURE:
( A ) NAME/KEY: Modified-site
( B ) LOCATION: 13
( D ) OTHER INFORMATION: /note= "Peptide is amidated at C- terminus."

( x i ) SEQUENCE DESCRIPTION: SEQ ID NO:18:

Gly Arg Arg Gly Arg Arg Gly Arg Gly Asp Ile Pro Thr
1 5 10

( 2 ) INFORMATION FOR SEQ ID NO:19:

( i ) SEQUENCE CHARACTERISTICS:
( A ) LENGTH: 11 amino acids
( B ) TYPE: amino acid
( D ) TOPOLOGY: linear ( i x ) FEATURE:
( A ) NAME/KEY: Modified-site
( B ) LOCATION: 11
( D ) OTHER INFORMATION: /note= "Peptide is amidated at C- terminus."

( x i ) SEQUENCE DESCRIPTION: SEQ ID NO:19:

Gly Arg Arg Gly Arg Arg Gly Arg Gly Asp Thr
1 5 10

( 2 ) INFORMATION FOR SEQ ID NO:20:

( i ) SEQUENCE CHARACTERISTICS:
( A ) LENGTH: 12 amino acids
( B ) TYPE: amino acid
( D ) TOPOLOGY: linear ( i x ) FEATURE:
( A ) NAME/KEY: Modified-site
( B ) LOCATION: 12
( D ) OTHER INFORMATION: /note= "Peptide is amidated at C- terminus."

( x i ) SEQUENCE DESCRIPTION: SEQ ID NO:20:

Gly Arg Arg Gly Arg Arg Gly Arg Gly Asp Ile Thr
1 5 10

( 2 ) INFORMATION FOR SEQ ID NO:21:

( i ) SEQUENCE CHARACTERISTICS:
( A ) LENGTH: 12 amino acids
( B ) TYPE: amino acid
( D ) TOPOLOGY: linear ( i x ) FEATURE:
( A ) NAME/KEY: Modified-site
( B ) LOCATION: 12
( D ) OTHER INFORMATION: /note= "Peptide is amidated at C- terminus."

( x i ) SEQUENCE DESCRIPTION: SEQ ID NO:21:

Arg Arg Gly Arg Arg Gly Arg Gly Asp Ile Pro Thr
1 5 10

( 2 ) INFORMATION FOR SEQ ID NO:22:

( i ) SEQUENCE CHARACTERISTICS:
( A ) LENGTH: 11 amino acids
( B ) TYPE: amino acid
( D ) TOPOLOGY: circular ( i x ) FEATURE:
( A ) NAME/KEY: Peptide ( B ) LOCATION: 2
( D ) OTHER INFORMATION: /note= "Xaa = (Pen)"

( i x ) FEATURE:
( A ) NAME/KEY: Disulfide-bond
( B ) LOCATION: 2..10
( D ) OTHER INFORMATION: /note= "Peptides cyclized between Pen and Cys."

( x i ) SEQUENCE DESCRIPTION: SEQ ID NO:22:

Lys Xaa Gly Phe Arg Gly Asp Thr Pro Cys Arg
1 5 10

( 2 ) INFORMATION FOR SEQ ID NO:23:

( i ) SEQUENCE CHARACTERISTICS:
( A ) LENGTH: 11 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa = (Pmc)."

( i x ) FEATURE:
( A ) NAME/KEY: Disulfide-bond
( B ) LOCATION: 2..10
( D ) OTHER INFORMATION: /note= "Peptides cyclized between Pmc and Cys."

( x i ) SEQUENCE DESCRIPTION: SEQ ID NO:23:

Arg Xaa Gly His Arg Gly Asp Arg Arg Cys Arg
1 5 10

( 2 ) INFORMATION FOR SEQ ID NO:24:

( i ) SEQUENCE CHARACTERISTICS:
( A ) LENGTH: 10 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa = (Pen)"

( i x ) FEATURE:
( A ) NAME/KEY: Disulfide-bond
( B ) LOCATION: 2..9
( D ) OTHER INFORMATION: /note= "Peptides cyclized between Pen and Cys."

( x i ) SEQUENCE DESCRIPTION: SEQ ID NO:24:

Arg Xaa His Arg Gly Asp Trp Arg Cys Arg
1 5 10

( 2 ) INFORMATION FOR SEQ ID NO:25:

( i ) SEQUENCE CHARACTERISTICS:
( A ) LENGTH: 10 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa = (Pen)"

( i x ) FEATURE:
( A ) NAME/KEY: Disulfide-bond
( B ) LOCATION: 2..9
( D ) OTHER INFORMATION: /note= "Peptides cyclized between Pen and Cys."

( x i ) SEQUENCE DESCRIPTION: SEQ ID NO:25:

Arg Xaa Pro Arg Gly Asp Trp Arg Cys Arg
1 5 10

( 2 ) INFORMATION FOR SEQ ID NO:26:

( i ) SEQUENCE CHARACTERISTICS:
( A ) LENGTH: 11 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa = Pen"

( i x ) FEATURE:
( A ) NAME/KEY: Disulfide-bond
( B ) LOCATION: 2..10
( D ) OTHER INFORMATION: /note= "Peptides cyclized between Pen and Cys."

( x i ) SEQUENCE DESCRIPTION: SEQ ID NO:26:

Gly Xaa Ala Ala Arg Gly Asp Asn Pro Cys Ala
1 5 10

( 2 ) INFORMATION FOR SEQ ID NO:27:

( i ) SEQUENCE CHARACTERISTICS:
( A ) LENGTH: 11 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa = (Pen)"

( i x ) FEATURE:
( A ) NAME/KEY: Disulfide-bond
( B ) LOCATION: 2..10
( D ) OTHER INFORMATION: /note= "Peptides cyclized between Pen and Cys."

( x i ) SEQUENCE DESCRIPTION: SEQ ID NO:27:

Gly Xaa Arg Ala Arg Gly Asp Asn Arg Cys Ala
1 5 10

( 2 ) INFORMATION FOR SEQ ID NO:28:

( i ) SEQUENCE CHARACTERISTICS:
( A ) LENGTH: 10 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa = (Pen)"

( i x ) FEATURE:
( A ) NAME/KEY: Disulfide-bond
( B ) LOCATION: 2..8
( D ) OTHER INFORMATION: /note= "Peptides cyclized between Pen and Cys."

( x i ) SEQUENCE DESCRIPTION: SEQ ID NO:28:

Gly Xaa Phe Arg Gly Asp Phe Cys Ala Lys
1 5 10

( 2 ) INFORMATION FOR SEQ ID NO:29:

( i ) SEQUENCE CHARACTERISTICS:
( A ) LENGTH: 12 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa = (Pen)"

( i x ) FEATURE:
( A ) NAME/KEY: Disulfide-bond
( B ) LOCATION: 2..10
( D ) OTHER INFORMATION: /note= "Peptides cyclized between Pen and Cys."

( x i ) SEQUENCE DESCRIPTION: SEQ ID NO:29:

Gly Xaa Arg Ala Arg Gly Asp Asn Pro Cys Ala Lys
1 5 10

( 2 ) INFORMATION FOR SEQ ID NO:30:

( i ) SEQUENCE CHARACTERISTICS:
( A ) LENGTH: 21 amino acids
( B ) TYPE: amino acid
( D ) TOPOLOGY: circular ( i x ) FEATURE:
( A ) NAME/KEY: Peptide
( B ) LOCATION: 2..6
( D ) OTHER INFORMATION: /note= "Xaa = D-Arginine (dR)"

( i x ) FEATURE:
( A ) NAME/KEY: Peptide
( B ) LOCATION: 10
( D ) OTHER INFORMATION: /note= "Xaa = (Pen)"

( i x ) FEATURE:
( A ) NAME/KEY: Disulfide-bond
( B ) LOCATION: 10..17
( D ) OTHER INFORMATION: /note= "Peptides cyclized between Pen and Cys."

( x i ) SEQUENCE DESCRIPTION: SEQ ID NO:30:

Gly Xaa Xaa Xaa Xaa Xaa Gly Gly Gly Xaa Phe Arg Gly Asp Ser Phe
1 5 10 15

Cys Ala Ser Ser Lys
20

( 2 ) INFORMATION FOR SEQ ID NO:31:

( i ) SEQUENCE CHARACTERISTICS:
( A ) LENGTH: 10 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa = (Pen)"

( i x ) FEATURE:
( A ) NAME/KEY: Disulfide-bond
( B ) LOCATION: 2..9
( D ) OTHER INFORMATION: /note= "Peptides cyclized between Pen and Cys."

( x i ) SEQUENCE DESCRIPTION: SEQ ID NO:31:

Arg Xaa Phe Arg Gly Asp Thr Pro Cys Lys
1 5 10